United States Patent [19]
Hotchkiss et al.

[11] Patent Number: 5,376,091
[45] Date of Patent: * Dec. 27, 1994

[54] DYNAMIC FINGER SUPPORT

[75] Inventors: Robert N. Hotchkiss, Riverside, Conn.; Kenneth W. Hotchkiss, Golden; Arthur Woodward, Lakewood, both of Colo.

[73] Assignee: Smith & Nephew Richards, Inc., Memphis, Tenn.

[*] Notice: The portion of the term of this patent subsequent to Mar. 31, 2009 has been disclaimed.

[21] Appl. No.: 225,498

[22] Filed: Apr. 11, 1994

Related U.S. Application Data

[63] Continuation of Ser. No. 859,262, Mar. 25, 1992, Pat. No. 5,100,403, which is a continuation-in-part of Ser. No. 535,170, Jun. 8, 1990, abandoned, and Ser. No. 696,358, May 6, 1991, abandoned.

[51] Int. Cl.$^5$ .............................. A61F 5/00
[52] U.S. Cl. ......................... 606/55; 606/54; 606/58; 606/59; 602/22; 602/37
[58] Field of Search ............ 602/5, 16, 20–22, 602/36, 37; 606/54–59

[56] References Cited

U.S. PATENT DOCUMENTS

| | | |
|---|---|---|
| 2,767,708 | 10/1956 | Keropian . |
| 2,832,334 | 4/1958 | Whitelaw . |
| 3,631,542 | 1/1972 | Potter . |
| 3,976,057 | 8/1976 | Barclay . |
| 4,019,504 | 4/1977 | Sterling . |
| 4,100,919 | 7/1978 | Oganesyan et al. ............ 606/56 |
| 4,220,334 | 9/1980 | Kanamoto et al. . |
| 4,488,542 | 12/1984 | Helland . |
| 4,604,997 | 8/1986 | De Bastiani et al. . |
| 4,611,586 | 9/1986 | Agee . |
| 4,612,919 | 9/1986 | Best . |
| 4,643,177 | 2/1987 | Sheppard et al. . |
| 4,651,719 | 3/1987 | Funk et al. . |
| 4,679,548 | 7/1987 | Pecheux . |
| 4,696,293 | 9/1987 | Ciullo . |
| 4,718,665 | 1/1988 | Airy et al. . |
| 4,719,906 | 1/1988 | De Prospero . |
| 4,724,827 | 2/1988 | Schenck . |
| 4,765,320 | 8/1988 | Lindemann et al. . |
| 4,782,842 | 11/1988 | Fietti . |
| 5,100,403 | 3/1992 | Hotchkiss et al. . |

FOREIGN PATENT DOCUMENTS

| | | |
|---|---|---|
| 0078093 | 5/1983 | European Pat. Off. . |
| 0460944 | 12/1991 | European Pat. Off. . |
| 2559379 | 2/1985 | France . |
| 2576512 | 8/1986 | France . |
| 2614782 | 11/1988 | France . |
| 3026839 | 2/1982 | Germany . |
| 589416 | 6/1947 | United Kingdom . |
| 620952 | 4/1949 | United Kingdom . |
| 2110094 | 6/1983 | United Kingdom . |
| 367858 | 1/1973 | U.S.S.R. . |
| 959769 | 9/1982 | U.S.S.R. . |
| 1398853 | 5/1988 | U.S.S.R. . |

OTHER PUBLICATIONS

Morrey, B. F., *Journal of Bone and Joint Surgery*, 72-A:601–618, 1990, "Post-Traumatic Contracture of the Elbow".

Volkov, et al., *Journal of Bone and Joint Surgery*, 57-A:591–600, 1975, "Restoration of Function in the Knee and Elbow with a Hinge-Distractor Apparatus".

*Primary Examiner*—Stephen R. Crow
*Assistant Examiner*—Linda C. M. Dvorak
*Attorney, Agent, or Firm*—Pravel, Hewitt, Kimball & Krieger

[57] ABSTRACT

A dynamic joint support having proximal and distal support sections and means for rigidly connecting each support section to bone and a pair of hinges connecting each support section to each other and pivoting at the joint to cause movement of the support section and its corresponding attached bone through the movements of flexion and extension. The hinge may be driven in its movement by a gear mechanism which may be disengaged by means of a clutch. The dynamic joint support may also include a distraction mechanism for movement of the bones out of contact in the joint, while allowing for an active range of motion at the joint.

18 Claims, 12 Drawing Sheets

*FIG.17*
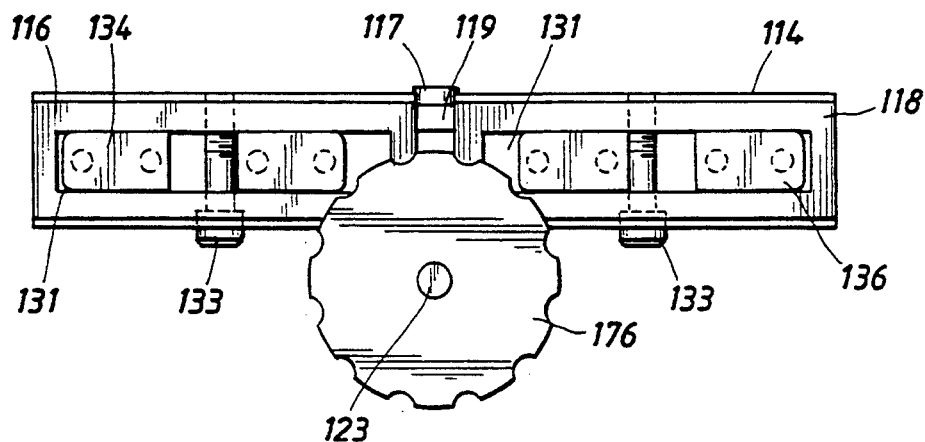
*FIG.18*
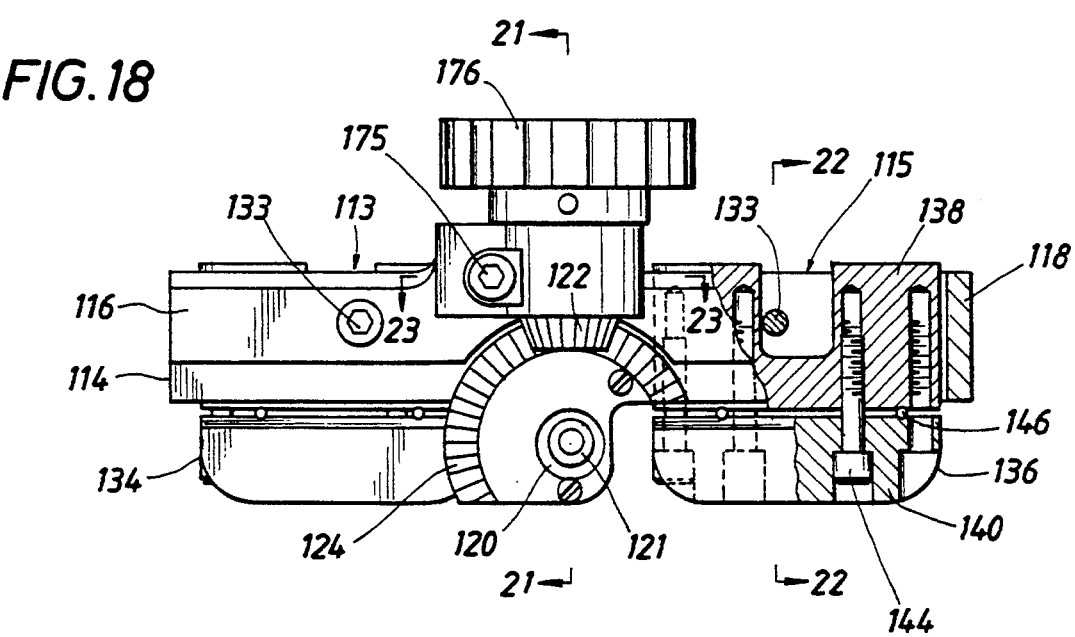
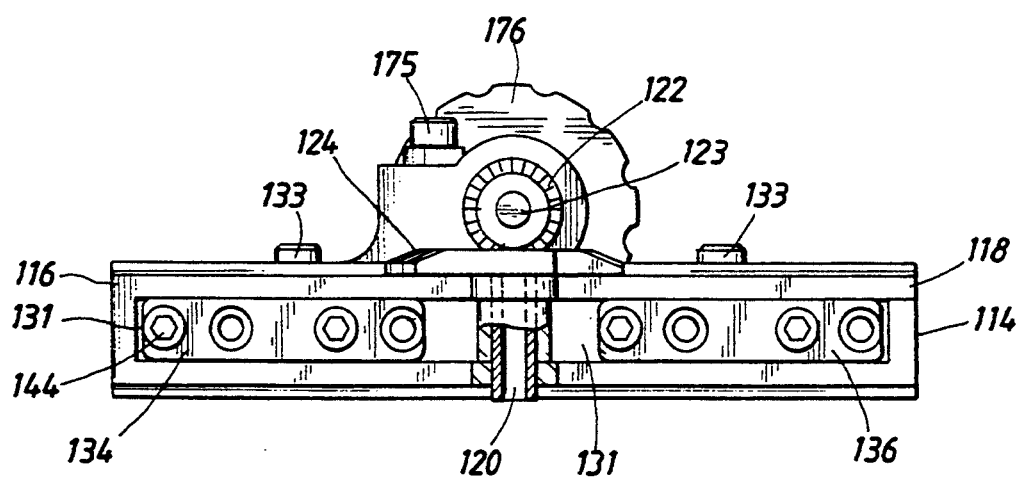
*FIG.19*

DYNAMIC FINGER SUPPORT

This is a continuation of co-pending application Ser. No. 07/859,262 filed on Mar. 25, 1992 now U.S. Pat. No. 5,100,403, and which is a continuation-in-part of Ser. No. 07/535,170 filed Jun. 8, 1990 and Ser. No. 07/696,358 filed May 6, 1991, both now abandoned.

FIELD OF THE INVENTION

The present invention relates generally to the treatment of injuries and contractures of a skeletal joint and, more particularly, to a dynamic finger support for allowing the proximal interphalangeal (PIP) joint to be flexed and extended either by the patient actively or passively or by a continuous passive motion machine and maintain its alignment in the natural axis of rotation for managing contractures and joint instability.

BACKGROUND OF THE INVENTION

Flexion contractures or a tendency for muscles, tendons or scar tissue to shorten in skeletal joints are common after trauma and represent a major challenge in the care of such injuries. For example, a contracture of 30°–40° in the elbow can severely reduce upper extremity function.

Contracture and stiffness of the finger joints due to trauma, burns, or arthritis limits the overall function of the hand. Motion of the proximal interphalangeal joint of the finger is especially important, as this joint accounts for more than 50% of the total active motion of the finger.

Current approaches to the treatment of joint trauma have more aggressively sought to prevent contracture and stiffness through movement. Methods of rigid internal fixation with sufficient stability to allow motion within days after injury rather than closed treatment and immobilization in a cast have been developed. In the treatment of dislocations, protected early motion is now begun as soon as the patient is comfortably able to do so.

However, the currently available techniques for the prevention of contracture are not uniformly successful. Early active motion alone can reduce the severity of contracture, but requires the patient's own strength, compliance and constant effort and proper alignment and tracking of the joint cannot be insured. Passive stretching by a therapist can be done on a very limited basis and is applied slowly, but such therapy risks the formation of heterotopic bone and myositis ossifications. Passive stretching is not generally useful at the PIP joint, as it is painful and not uniformly successful. Dynamic splints may be used, but these require pressure on the sometimes sensitive or injured soft tissues, e.g. of the arm and forearm, and may not be possible, i.e. burn injury, or may reduce patient compliance. Examples of such splinting devices include a turnbuckle orthosis or cast, reverse dynamic sling, polycentric cast brace hinges, or a hinged orthoses with rubber band traction.

Continuous passive motion (CPM) devices have been developed which provide early motion gains, but these devices do not normally allow the joint to come to the extremes of motion which are the areas of greatest need. Further, these devices are not designed to insure accurate tracking or stability of the joint, but instead for example, in the elbow device, move the wrist relative to the shoulder or the humerus. These devices also rely on direct pressure on the soft tissues and skin, and thus are subject to the same limitations as the external splints discussed above.

Flexion-extension hinge distractors are hinged external fixators which are designed to hold the joints such as the elbow in distraction while permitting an active range of motion. These include the Volkov elbow hinge-distractor and the Deland and Walker hinge distractor. These devices require the placement of a pin or wire into or in close proximity to the kinematic axis of the elbow, with the pin acting as the mechanical axis of the device. Because these devices are difficult to align over the axis of rotation, pin tracking problems can occur. Furthermore, the mechanical axis cannot be realigned without reinsertion of the pin. In addition, these systems do not permit passive driving of the joint through a range of motion.

An additional problem associated with the flexion-fixation hinge distractors is the placement of pins in close proximity to the joint. Because of the movement of skin over and relative to underlying bone, movement of the skin in this area with normal flexion and extension of the joint in relation to a stationary pin can cause skin irritation and lead to infection. Such placement of the pins may also interfere with the treatment of a fracture by internal fixation.

Contracture and stiffness of the finger joints after trauma is currently prevented by immediate physical therapy of the involved digit. However, it is often difficult to achieve full active motion of the finger because soft tissue swelling and pain prevent the patient from maximal compliance during the critical first weeks of healing. If motion of the injured PIP joint is not initiated and maximized, scar formation around the joint becomes very strong. Later attempts to gain motion at the joint are then prevented by the strength of the scar tissue and the mechanical disadvantage of the passive splint or exercise program. Bony injury or joint instability often precludes actively or passively moving the digit through an effective range of motion, because motion risks redislocation or displacement of the skeletal elements on either side of the joint, or of the joint itself.

Because of limitations with the currently available methods to prevent or treat joint injuries, patients often require surgical soft tissue release to improve the range of motion. Surgical release of contracture must be followed by many months of intensive therapy and splinting to maintain the gains in motion. Such maintenance is not uniformly successful, as the splinting and traditional therapies applied suffer from the same limitations as discussed above. Moreover, oftentimes the cost of surgery and therapy, as well as the costs in time, lost wages and rehabilitation can be significant.

SUMMARY OF THE INVENTION

In order to solve the problems described above, a dynamic joint support is provided which includes proximal and distal external bracing sections, respectively connected to proximal and distal skeletal elements on opposite sides of a joint. The bracing sections are rigidly connected to their respective skeletal elements through wires or pins, e.g., in the dynamic finger support, through a clamping member which engages pins inserted into integral bone.

A hinge connects the bracing sections to each other in the vicinity of the joint so that the hinge can pivot at the joint when the skeletal elements are moved through flexion or extension. The hinge includes an X-ray transparent material at the pivot point with a target mechanism, e.g., cross hairs, so the mechanical axis of the hinge can be aligned with the natural axis of the joint.

Appropriate adjusters are included with the external bracing sections for adjusting the length and orientation of the bracing sections relative to their respective skeletal elements and to the hinge for aligning the bracing sections relative to the joint. This alignment permits accurate placement of the axis of rotation of the device to recreate the normal kinematics of the joint.

The hinge also includes a gear mechanism which can be used for moving the bracing sections and consequently their respective skeletal elements relative to each other through the application of external force to the gear mechanism. The external force can be applied through a manually operated crank or a motor in order to stretch soft tissue surrounding the joint and thereby address a joint contracture. A clutch may also be provided so that the gear mechanism can be disengaged for allowing the skeletal elements to move freely under the patient's own muscle force through flexion and extension.

An adjustment mechanism can also be provided for placing the joint in distraction and maintaining its alignment in that position while the skeletal elements are moved through flexion and extension.

By providing the mechanism as described, contractures in the vicinity of a joint can be prevented through active or passive movement of the skeletal elements through the joint. Continuous passive motion can be applied to the joint with proper tracking and concomitant stability that comes from maintaining the skeletal elements in proper orientation relative to each other while they are being moved.

Further, the subject dynamic joint support also allows the joint to be held in distraction while permitting a range of motion without compression across the joint surfaces. All of the above can be performed without pins or wires in close proximity to the joint which eliminates skin irritation because there will be less skin motion relative to the underlying bone during movement. Further, the location of the pins is discretionary with the physician so that pins can be placed away from a fracture and not interfere with the healing process of a fracture in the vicinity of the joint. In addition, the apparatus may be designed to permit unrestricted access to the joint for medical and surgical procedures.

BRIEF DESCRIPTION OF THE DRAWINGS

A better understanding of the invention can be obtained from the detailed description of a preferred embodiment set forth below, when considered in conjunction with the appended drawings, in which:

FIG. 17 is a top plan view of the dynamic finger support.

FIG. 18 is a side plan view partially in section showing the attachment of the distal bracing section to the hinge.

FIG. 19 is a bottom plan view partially in section showing the engagement of the proximal and distal hinge members.

DETAILED DESCRIPTION OF THE INVENTION

Figure 1:
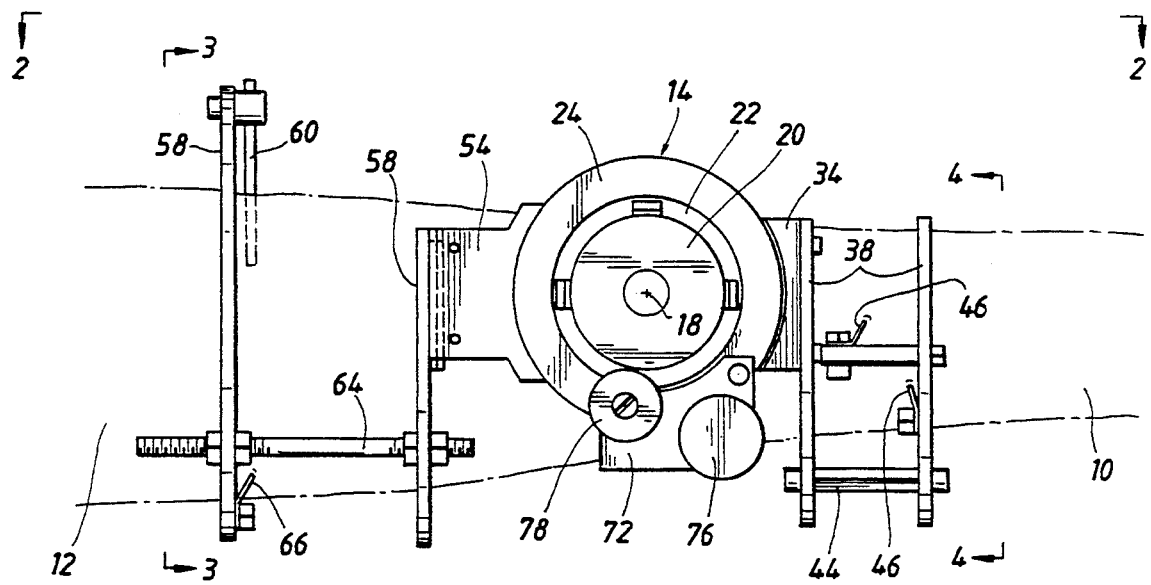
FIG. 1 is a side plan view of the dynamic elbow brace which is the subject of the present invention, as the brace would be connected to an arm of a patient in extension.
Figure 2:
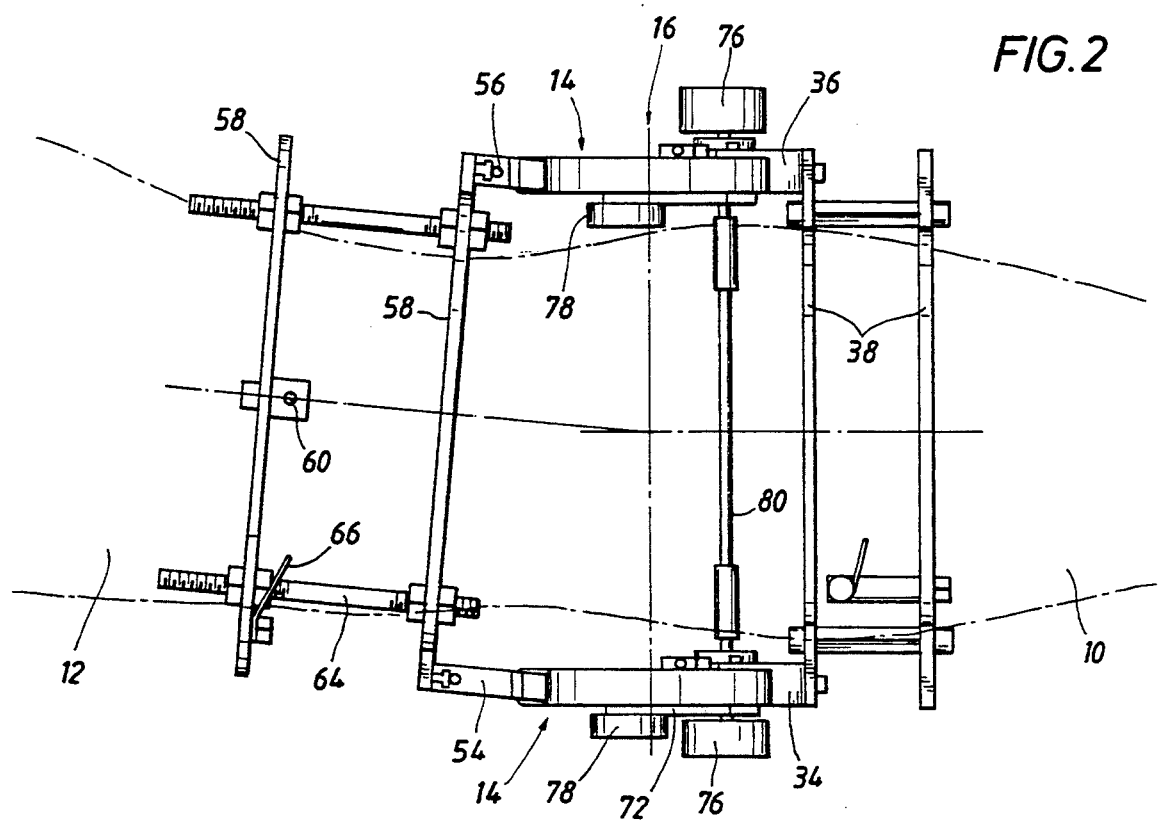
FIG. 2 is a bottom plan view of the dynamic elbow brace shown with a dashed line depiction of the axis of the underlying bones.

The dynamic joint support in a preferred embodiment of the present invention is shown as it would be connected to the arm of a patient in FIGS. 1 and 2, where reference numeral 10 identifies dashed lines illustrating the forearm of the patient and 12 the upper arm. The support includes a pair of hinges 14 which are collinear or aligned with the kinematic axis of the elbow as shown by center line 16 (see FIG. 2). This alignment can be accomplished through the use of an X-ray machine (not shown) which can center the hinge through radio-opaque cross hairs 18 provided in a central window 20 formed in the hinge 14, which is transparent to X-rays.

Figure 6:
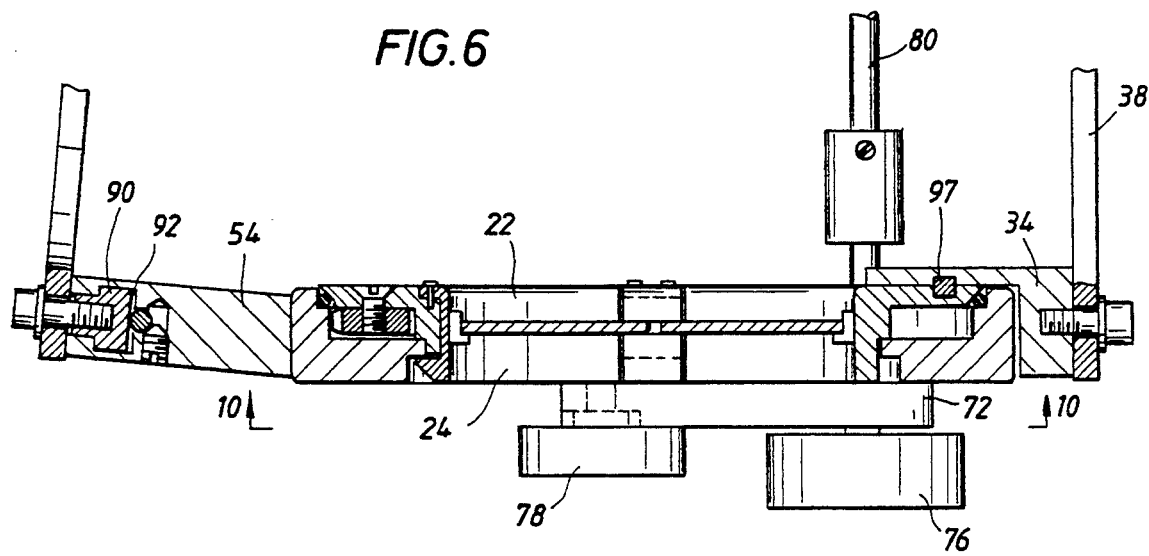
FIG. 6 is a top view of the proximal bracing section.
Figure 7:
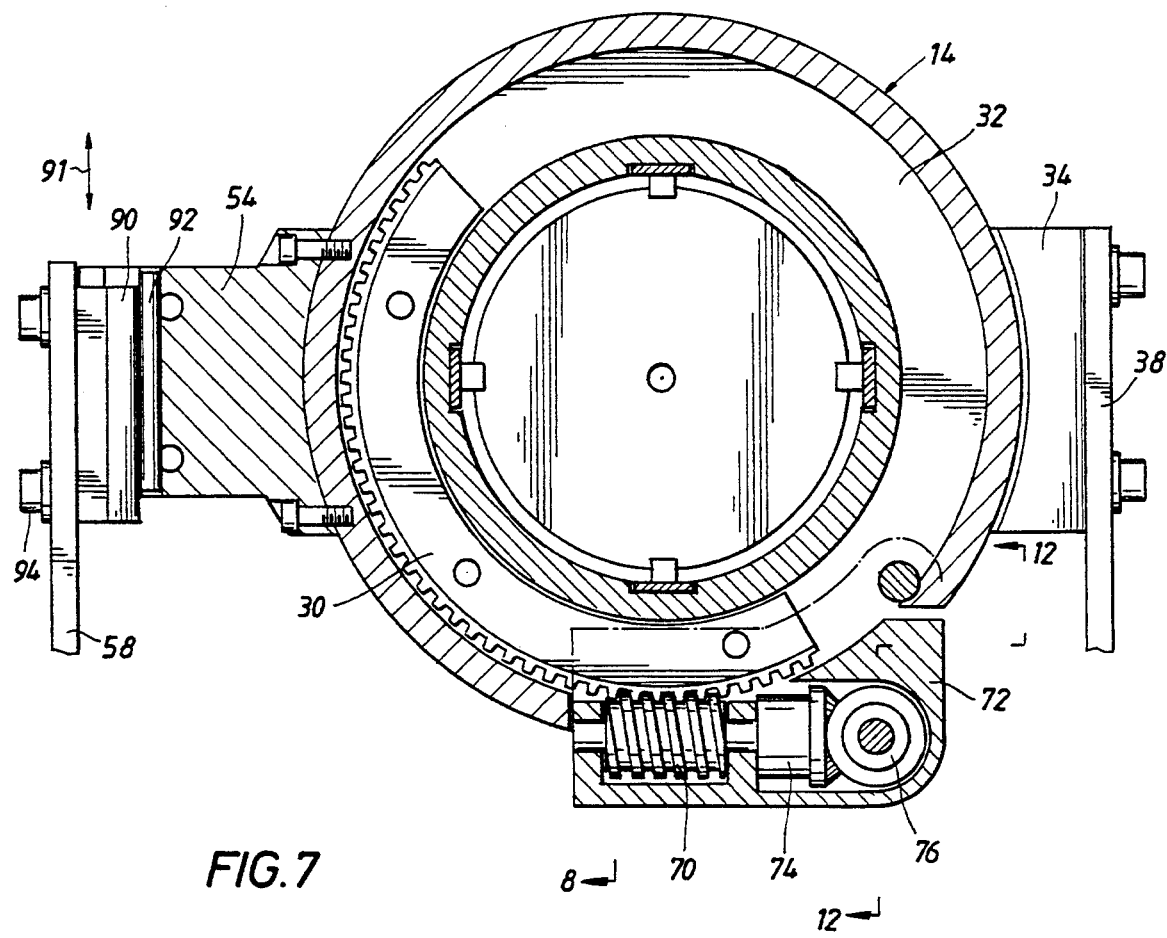
FIG. 7 is a side plan view partially in section of the hinge and the gear mechanism.
Figure 14:
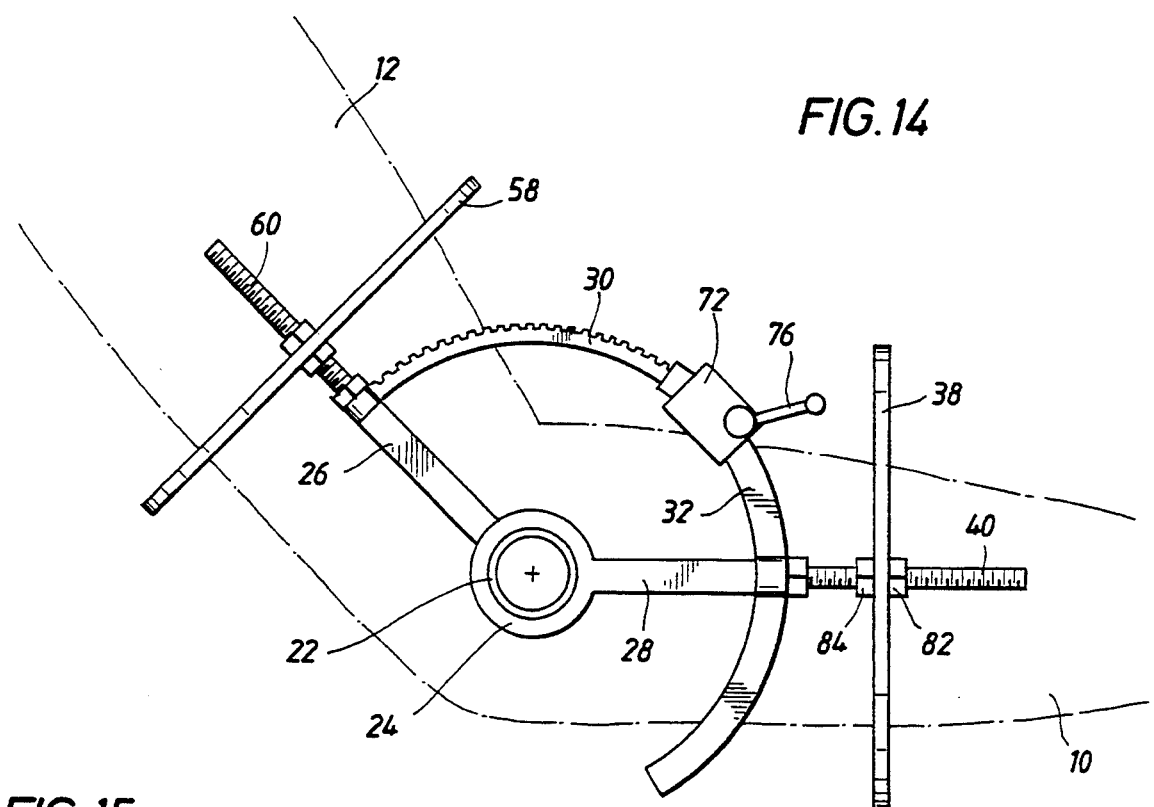
FIG. 14 is a side plan view of an alternative embodiment of the invention, as it would be attached to an arm in partial flexion.

Each hinge 14 includes a pair of fitted plates 24 which are adapted to rotate relative to each other and are respectively connected to arcuate members 30, 32 (FIG. 7). The connection of the rotating plates 22, 24 to the arcuate members 30,32 may be direct, as shown in FIGS. 6 and 7, or indirect, through radially-extending arms 26, 28 as shown in FIG. 14.

Referring again to FIGS. 1 and 2, distal adjustment blocks 34, 36 connect the hinges 14 to one or more annular support rings 38. Alternatively, as shown in FIG. 15, the hinges 14 may be connected to one or more annular support rings 38 by threaded rods 40.

Figure 3:
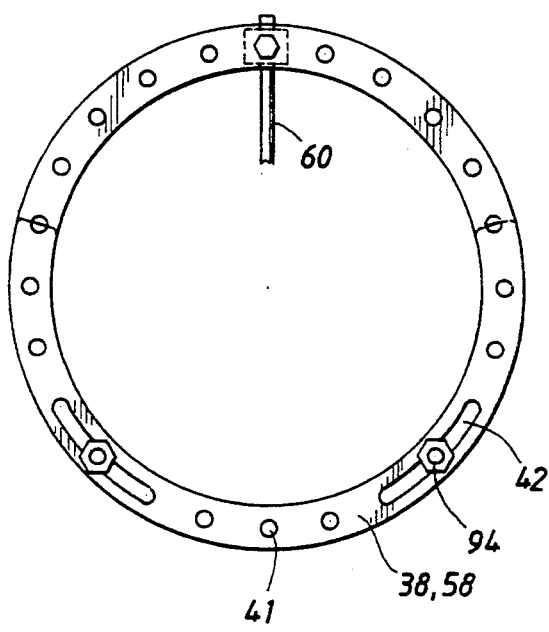
FIG. 3 is a partial plan view of a support ring, for fixing the support to the bone.
Figure 4:
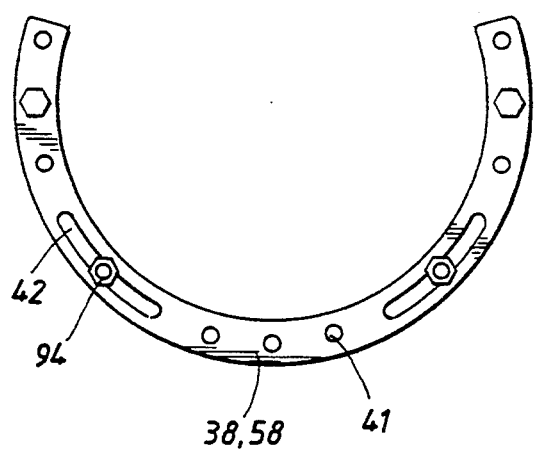
FIG. 4 is similar to FIG. 3, showing a support ring which only partially encircles the limb.

As shown in FIGS. 3 and 4, the annular support rings 38 may be formed in a closed or partial circle and contain a plurality of openings 41 around their circumference. The support rings 38, 58 can be similar to ones developed by Dr. Ilizarov for use in bone lengthening or rehabilitation techniques, which are commonly known as Ilizarov rings.

Rods 44 extend between the annular support rings 38 when more than one is used. Wires 46 or pins (not shown) attached to the annular support rings 38 or to the extending rods 44 are embedded in the ulna for holding the support ring 38 rigidly in place relative to the forearm 10. (While pins might likewise be placed in the radius, because of interference with the motions of supination and pronation, such placement is not preferred.)

Figure 15:
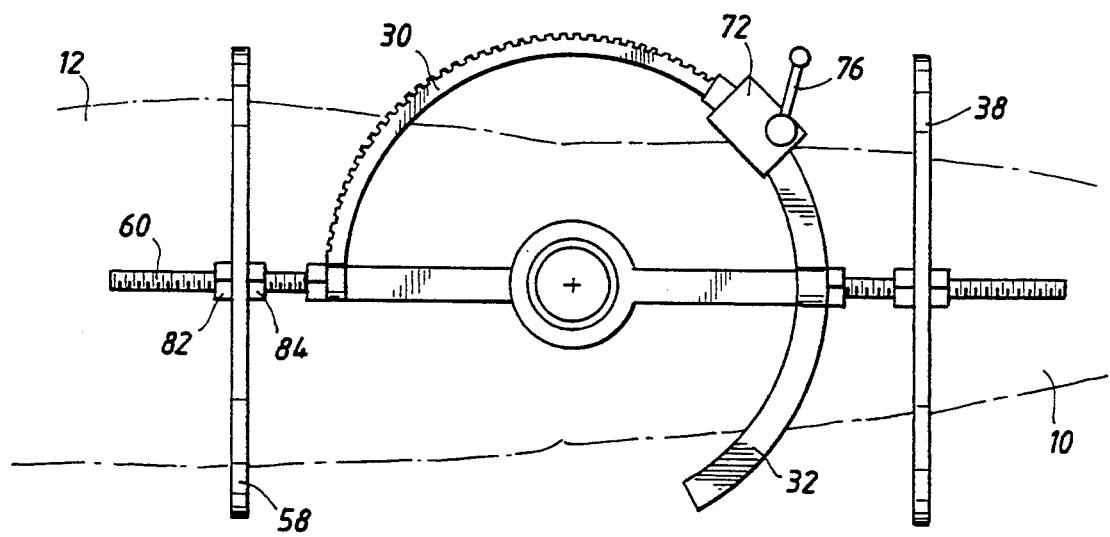
FIG. 15 is a similar view as FIG. 14, with the arm in extension.
Figure 16:
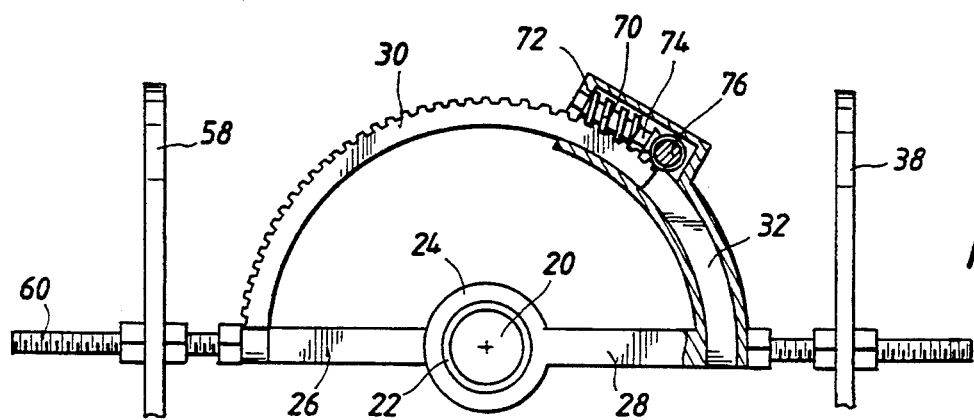
FIG. 16 is a side plan view partially in section showing the gear mechanism of the alternative embodiment.

Proximal adjustment blocks 54, 56 or rod 60 in the embodiment of FIGS. 14-16 likewise connect the hinges 14 to one or more annular support rings 58 which are connected to the humerus through a series of pins 60 or wires 66 which are in turn connected to the support rings 58 or through rods 64.

As shown in FIG. 2, the hinges 14 are located both medial and lateral to the elbow joint along with corresponding adjustment blocks 34, 36 and 54, 56. Also, arcuate members 30, 32 of the hinges 14 are located on both sides of the joint.

The hinges 14, the adjustment blocks 34, 36 and 54, 56, rods 44, 64 and the support rings 38, 58 form external bracing sections which can be connected to the respective bones in the forearm and upper arm. Through the hinges 14, these elements allow the arm of the patient to move between the extended position of FIG. 1, where the arm is relatively straight, and the flexed position of FIG. 5, where the forearm 10 and upper arm 12 are moved toward each other. As described in detail below, the bracing sections can be precisely aligned with the kinematic axis of the joint so that when the extension and flexion described above takes place, contractures are prevented, reduced or eliminated.

As shown best in FIG. 7, the arcuate member 30 is formed as a curved rack which mates with a worm 70 located in a housing 72 mounted on arcuate member 32. The housing 72 is hollow, to allow the curved rack 30 to telescope within the arcuate arm 32 as the worm 70 is moved through rotation of a miter gear 74. A crank 76 can be connected to the miter gear 74 which, when turned manually, will effect extension and flexion of the arm of the patient. Alternatively, a suitable connection can be provided for connecting a motor to the miter gear 74 for effecting continuous passive motion to the arm of the patient.

Figure 8:
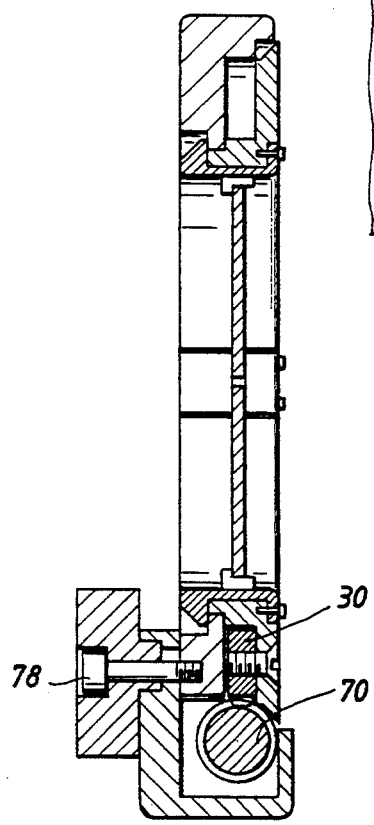
FIG. 8 is a top plan view partially in section showing the engaged clutch mechanism.
Figure 10:
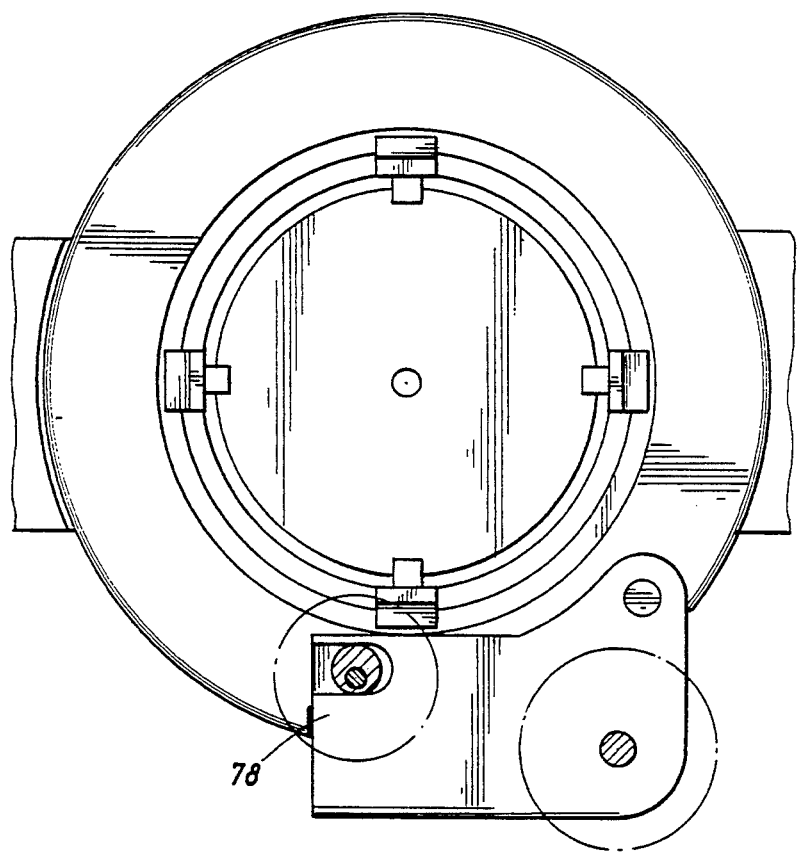
FIG. 10 is a perspective view of the hinge showing the clutch mechanism.
Figure 9:
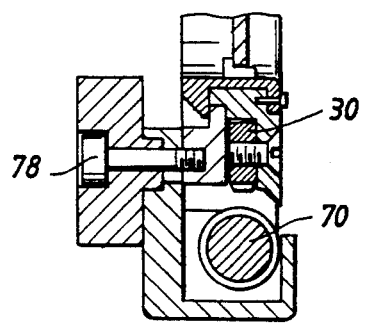
FIG. 9 is a top plan view partially in section showing the disengaged clutch mechanism.
Figure 11:
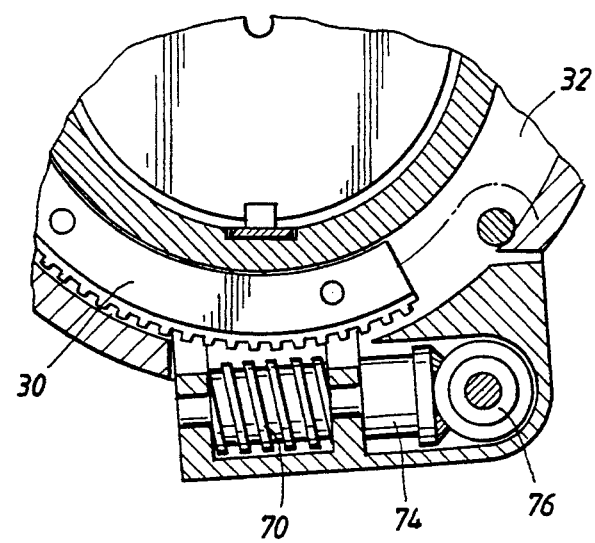
FIG. 11 is a sectional view of the disengaged gear mechanism.

Referring now to FIGS. 8 and 9, a clutch 78 can be provided for selectively disengaging the curved rack 30 from the worm mechanism 70 so that the patient can use his or her own power to extend or flex the arm. The clutch 78 may be for example, a set screw or crank which, when engaged, as showing in FIG. 8, causes the curved rack 30 to engage the worm 70. When the clutch 78 is disengaged, as shown in FIGS. 9 and 11, the curved rack 30 is disengaged from contact with the worm 70, and permits free movement of the arcuate members 30, 32 relative to each other.

Figure 12:
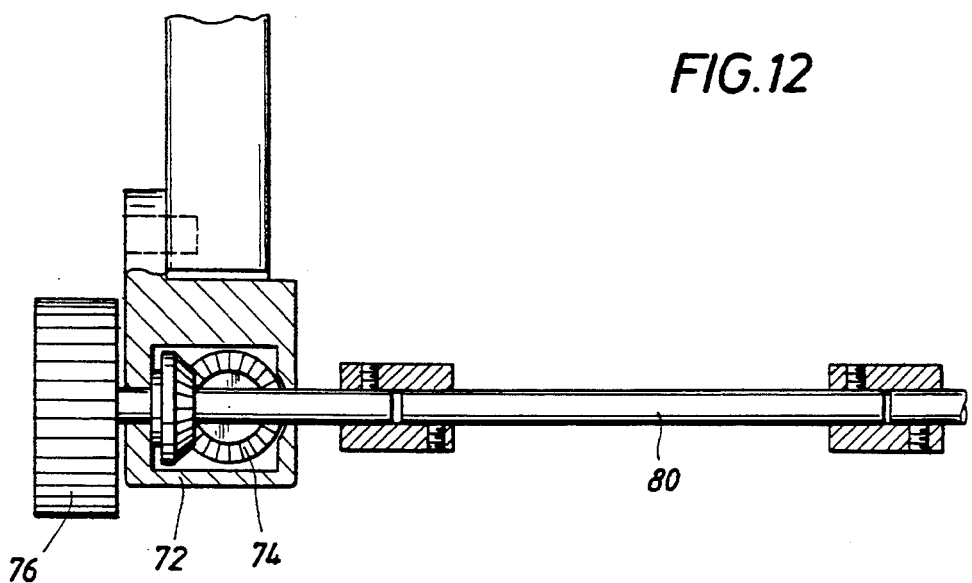
FIG. 12 is a plan view partially in section of the gear mechanism and the drive shaft.

The arcuate members 30, 32 on the opposing sides of the elbow joint can each move relative to each other as described above. Only one hinge of the two opposing hinges on each side of the joint requires the gearing mechanism as described. Referring to FIGS. 2 and 12, a drive shaft 80 is connected between the gear housing 72 of each hinge 14, and transfers rotational energy from one hinge to the opposite hinge. Turning of the crank 76 of one hinge thus drives each hinge in synchrony through the drive shaft 80.

The drive shaft 80 may extend between the hinges either anterior or posterior to the joint. Because of the incidence of anterior swelling in trauma to the elbow joint, it is generally preferred that the drive shaft 80 be positioned posterior to the elbow joint. For ease of patient use, it may be preferred that the crank be located on the medial aspect of the elbow joint.

While only one gear mechanism is required, it is preferred that both hinges 14 contain the complete gear system. Having the gear mechanism available on each side of the joint provides more accurate tracking of the arcuate members 30, 32, allows the device to be interchangeable between right and left arms, and also allows maximal flexibility of patient and physician use. In the preferred embodiment, turning of one crank 76 provides rotational energy to the drive shaft 80, which provides rotational energy to the miter gears 74 and worms 70 of both hinges in synchrony.

Figure 5:
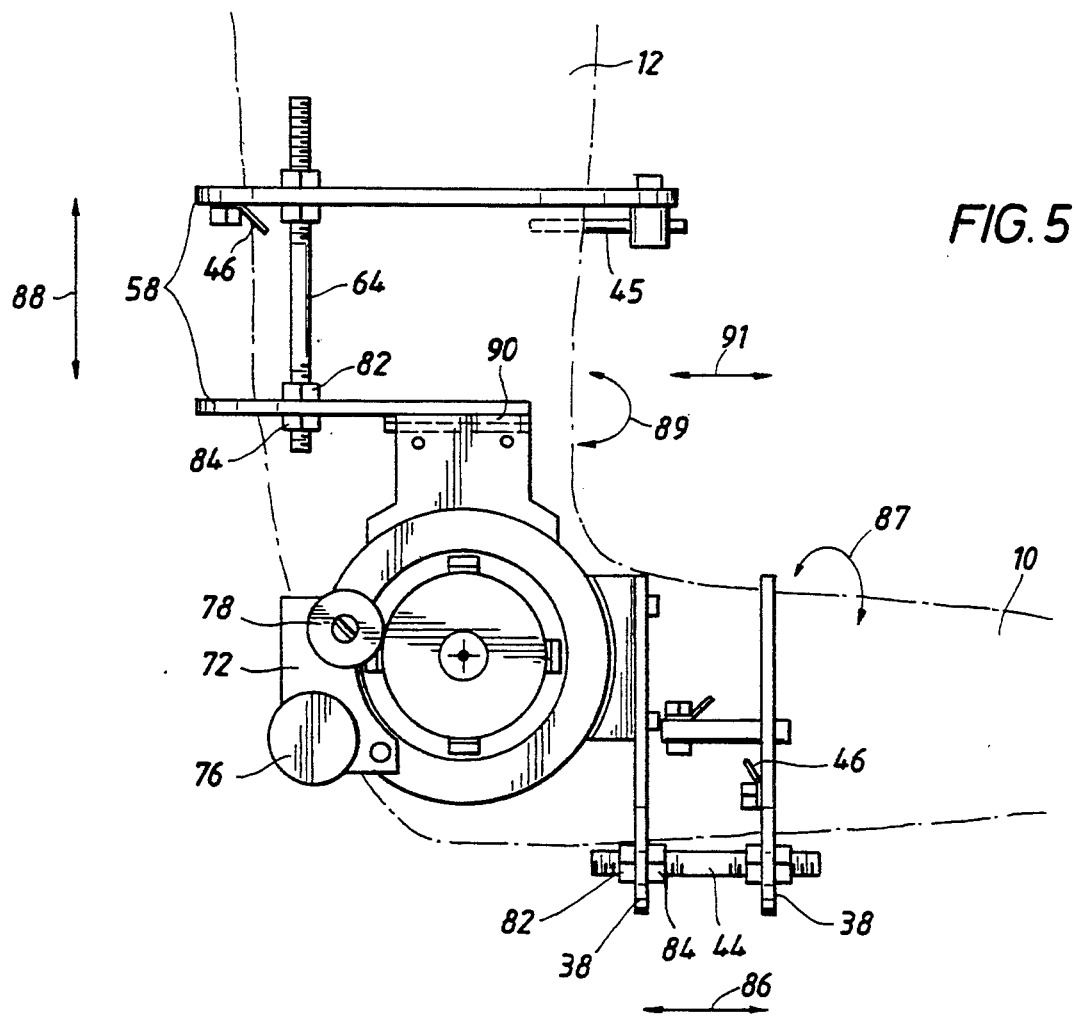
FIG. 5 is a side plan view of the dynamic elbow brace, as it would be connected to the arm of a patient in flexion.

Referring to FIG. 5, the dynamic support of the present invention is shown installed by first connecting the support rings 38, 58 to bones of the patient's arm using pins 45 or wires 46, with the remainder of the apparatus loosely connected and generally aligned. The proximal support ring 58 is oriented perpendicular to the proximal humerus of the arm 12, while the distal support ring 38 is oriented perpendicular to the ulna of the forearm 10. The extended rods 44, 64 are threaded with corresponding nuts 82, 84 so that the location of the hinge 14 can be adjusted in length relative to the support rings 38, 58 in the direction of arrows 86, 88.

As shown in FIGS. 3 and 4, openings 42 in the support rings 38, 58 are elongated so the hinge 14 can be adjusted circumferentially relative to the stabilized bone, as illustrated by arrows 87, 89 in FIG. 5. Rotational adjustments can be made as described above between the support ring 58 and the proximal adjustment blocks 54, 56 by way of the elongated slots 42 of the support ring 58. Once positioned rotationally, the support ring 58 is held tightly in place, for example, by tightening of screws 94 through the elongated slots 42 and into the adjustment block 54, 56.

The natural axis of the forearm of a patient 10 is offset from the axis of the upper arm 12 by approximately 7°. Proper alignment of the external support sections on opposite sides of the hinge is necessary in order to maintain the proper angle of the bones during extension and flexion. As shown in FIG. 2, to accommodate for this natural angle of the elbow joint, the lateral proximal adjustment block 54 is larger in size with respect to the medial proximal adjustment block 56. It is important that the variation in the medial and lateral blocks compensate for the 7° angle at the axis of the elbow joint.

It is contemplated that the device may be interchangeable between the right and left arms by exchanging the medial and lateral proximal adjustment blocks. It is also contemplated that proximal adjustment blocks of varied sizes may be substituted to compensate for variation in the distance between the hinges, for example, when treating a child versus an adult.

As shown in FIGS. 6 and 7, the proximal adjustment block 54, 56 includes a sliding block 90 and a track 92 in which the sliding block 90 slides to adjust the location of the hinge 14 in the anterior-posterior direction (arrow 91) relative to the proximal support ring 58 and thereby relative to the stabilized bone.

Figure 13:
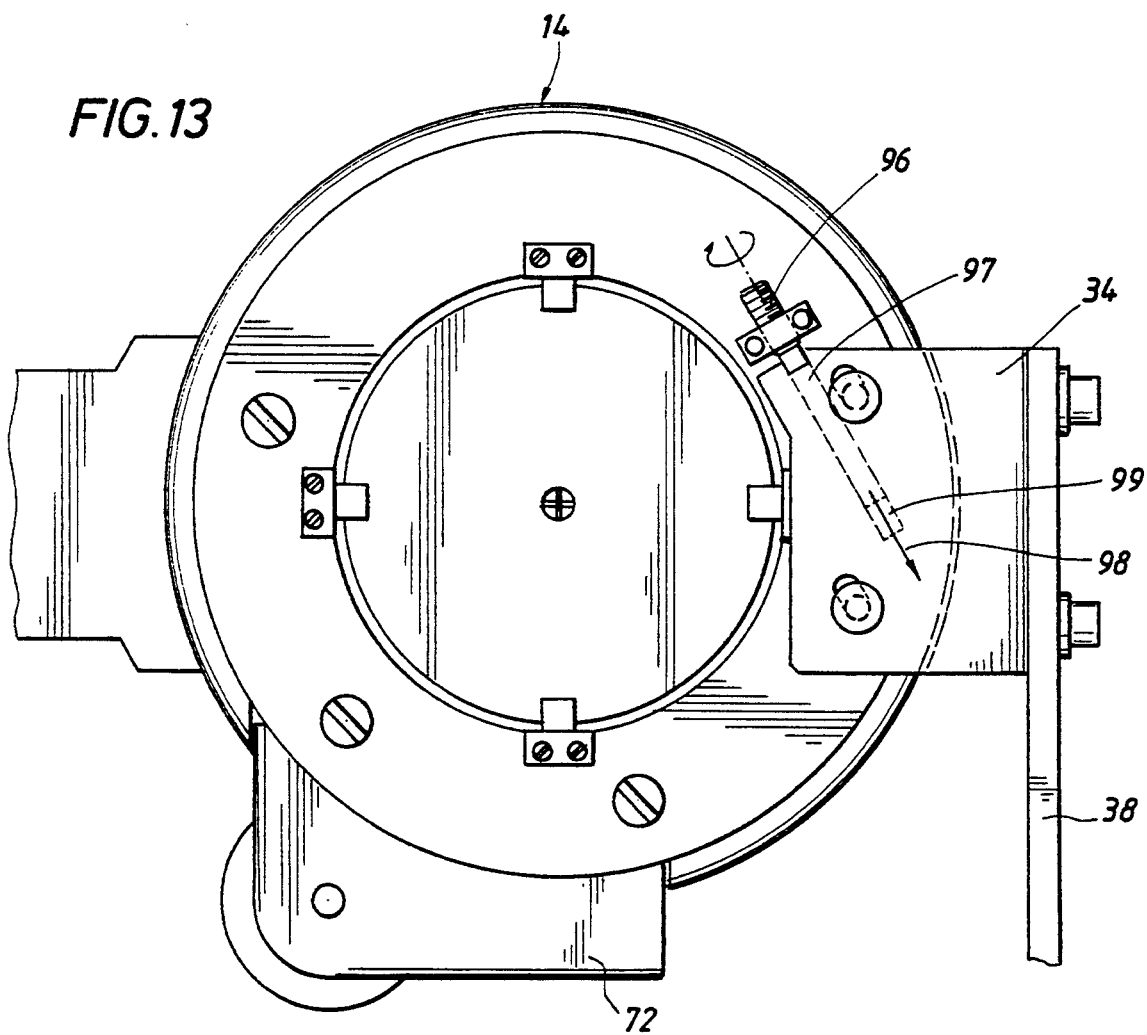
FIG. 13 is a side plan view of the hinge showing the distraction mechanism.

As shown in detail in FIG. 13, the distal support ring 38 is connected to the hinge 14 through the distal adjustment blocks 34, 36. When distraction of the joint is desired, the distal adjustment blocks 34, 36 allow the hinge 14 to be moved along a line about 30° relative to a line perpendicular to the bones of the forearm. This can be accomplished, for example, by turning a set screw 96 which moves a boss 97 in a track 99 to cause movement of the distal adjustment blocks 34, 36 along the line 98. This movement of the distal adjustment blocks allows the attached bones of the forearm to be distracted, or to be moved slightly out of contact with the humerus with the device, permitting motion of the joint during distraction. Distraction of the joint may be desired in treatment of injuries to the joint itself.

The dynamic joint support in an alternate preferred embodiment of the present invention is shown as it would be connected to the finger of a patient in FIGS. 24-27, where reference numeral 110 identifies dashed lines illustrating the proximal phalanx of the patient's finger and 112 the distal phalanx. The finger support includes a hinge 114 which is collinear or aligned with the kinematic axis of the PIP joint. This alignment can be accomplished through the use of a X-ray machine, preferably in video (not shown) which can be used to align the radiolucent hinge directly over the axis of the PIP joint, for example, using as a targeting mechanism a radiopaque axle.

Figure 20:
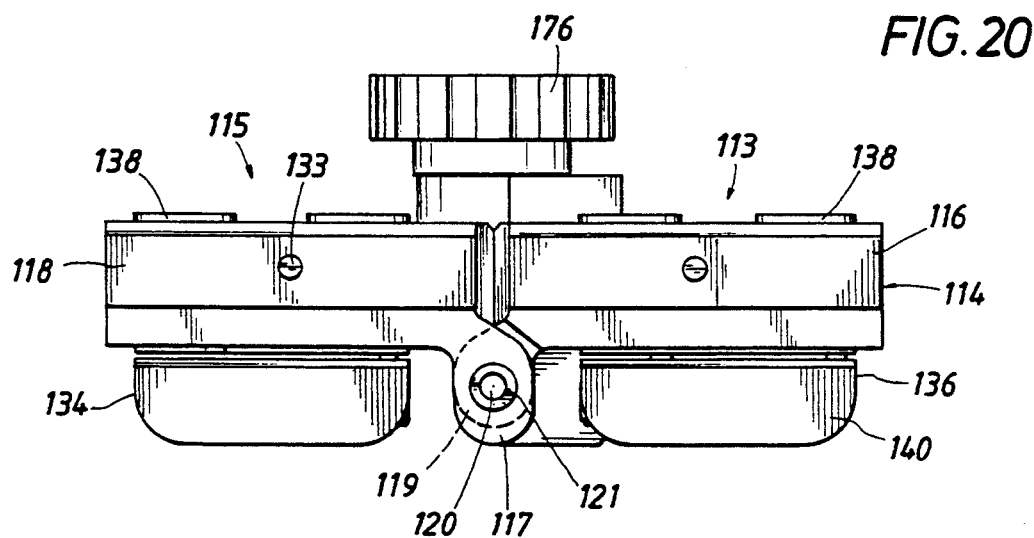
FIG. 20 is a side plan view of the dynamic finger support showing in dashed lines the pivotal engagement of the proximal and distal hinge members.

The dynamic finger support includes proximal and distal bracing sections 113, 115 which are adapted to rotate relative to one another, for example, as shown in FIG. 20, by pivoting joint 120 formed between a receiving member 117 and extending member 119. A radiopaque axle 121 may serve as the axis of rotation of the hinge 114, and provide a target for alignment of the radiotranslucent finger hinge with the natural axis of the joint.

Figure 25:
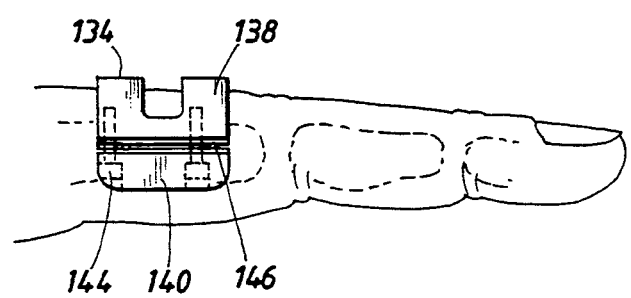
FIG. 25 is a side plan view of the proximal bracing section as connected to pins in the proximal phalanx of a patient.
Figure 28:
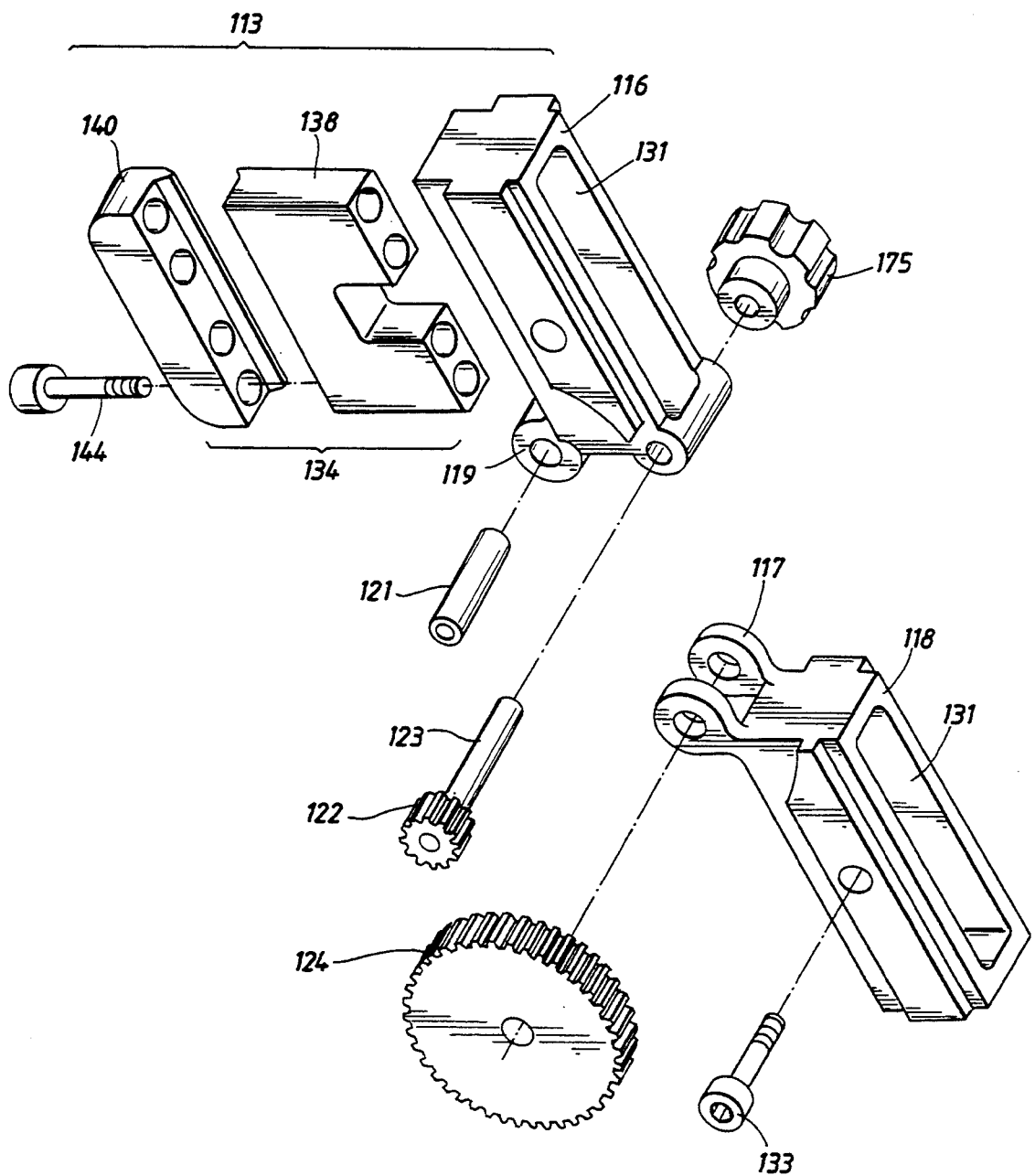
FIG. 28 is an exploded view of the dynamic finger support.

Each bracing section 113, 115 is adapted for attachment to pins 146 (see FIG. 24) or wires (not shown) embedded in the proximal and distal phalanges 110, 112. For example, as shown in FIGS. 18, 25, and 28, each bracing section 113, 115 includes a hinge member 116, 118 adapted to receive a clamping member 134, 136. Each clamping member 134, 136 is formed with upper and lower jaws 138, 140, which are joined and tightened, for example, by vertical screws 144 on the engaged pins 146. One or more vertical screws 144 may be positioned in the clamping member away from the engaged pins 146. It is preferred that the communicating portions of the jaws 138, 140 be adapted to tightly clamp together and around the engaged pins, for example, by a fitted or tapered edge on each communication surface.

Each hinge section 116, 118 is adapted to receive its respective clamping member 134, 136. For example, as shown in FIGS. 17, 19, 22 and 28, clamping members 134, 136 engage hinge sections 116, 118 through a cavity 131 in each hinge section. Once inserted into the cavity 131, a fastener, e.g., horizontal screw 133 through the hinge section 116, 118 fixes the clamping member 134, 136 to the hinge section 116, 118.

Figure 21:
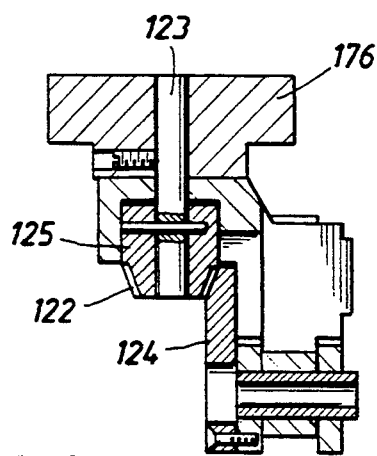
FIG. 21 is a sectional view along line 5 of FIG. 18 showing the gear mechanism, gear shaft and finger dial.
Figure 22:
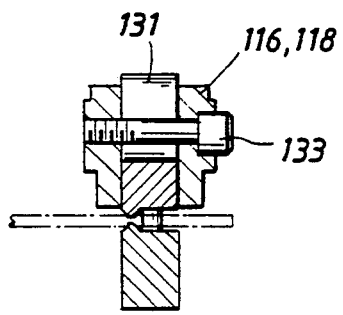
FIG. 22 is a sectional view along line 6 of FIG. 18 showing the engagement of the bracing section with the hinge member.

A drive means is provided to move the proximal and distal bracing sections relative to each other and about the axle. For example, as shown best in FIG. 18, the proximal hinge section 116 includes a first gear, e.g., a pinion 122 which mates with a second gear e.g., a fixed, curved rack 124 included in the distal hinge section 118. As shown in FIGS. 19 and 21, the first gear 122 is moved through rotation of a drive shaft 123 which translates rotational energy from the attached finger dial 176. When turned manually, the finger dial 176 will thus effect extension and flexion of the finger joint of the patient. As shown in FIGS. 18 and 28, the finger dial 176 and drive shaft 123 may be positioned perpendicular or normal to the axis of rotation.

Figure 23:
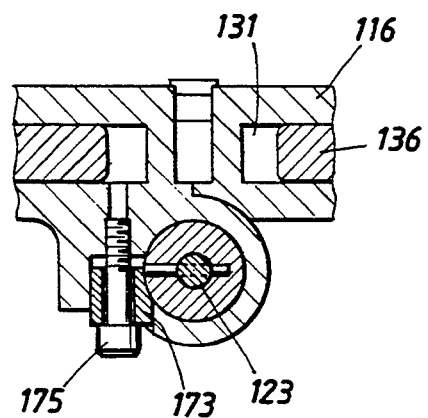
FIG. 23 is a sectional view along line 7 of FIG. 18 showing the gear means and locking means.
Figure 24:
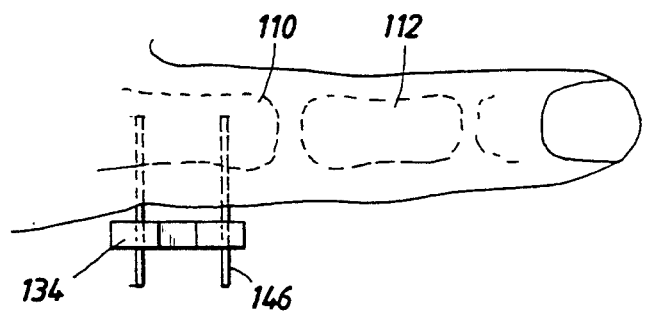
FIG. 24 is a top plan view of the proximal bracing section as connected to pins in the proximal phalanx of a patient.

As shown in FIGS. 18, 21 and 23 a locking means, e.g., set screw 175 can be provided for selectively locking or unlocking the relative position of the first and second gears. Tightening of the set screw 175 effects friction between a brake shoe 173 and the pinion 122 at a pinion collar 125, thereby causing a locked engagement of the gears, prohibiting relative movement of the gears. Releasing the gear screw 175 releases the friction and loosens the engagement and relative motion of the gears.

Figure 26:
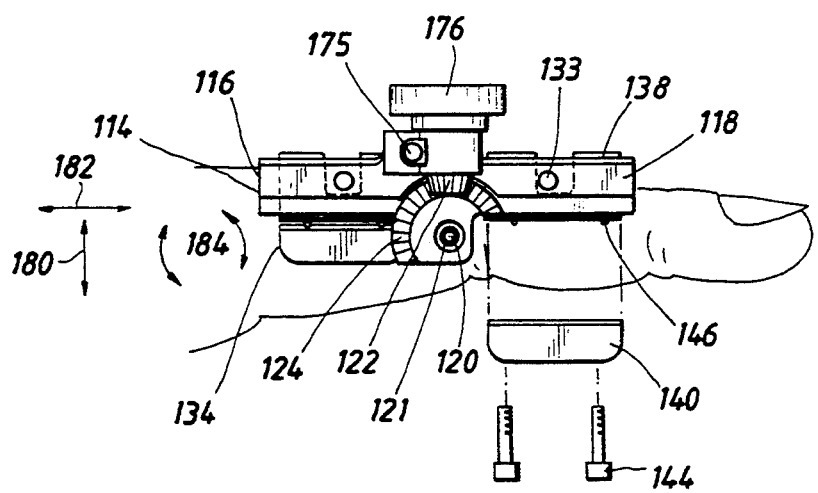
FIG. 26 is a side plan view of the device as attached to the finger of a patient in extension.
Figure 27:
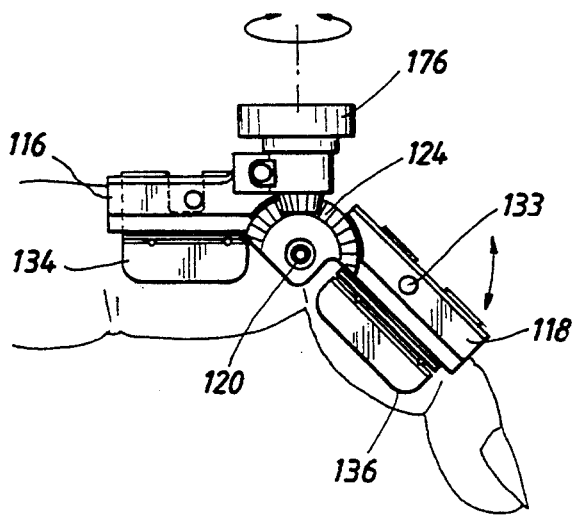
FIG. 27 is a side plan view of the device as attached to the finger of a patient in flexion.

The elements of the hinge 114, as fixed onto the clamping members 134, 136 and the attached skeletal elements 110, 112 as described above, allow the PIP joint of the finger of a patient to move between the extended position of FIG. 26, where the finger is relatively straight, and the flexed position of FIG. 27, where the proximal phalanx 110 and distal phalanx 112 are moved toward each other. As described in detail below, the hinge 114 can be adjusted to permit precise alignment with the kinematic axis of the joint so that when the extension and flexion described above takes place, contractures are prevented, reduced or eliminated.

Referring to FIG. 24-27, the installation of dynamic finger support of the present invention is shown. The proximal clamping member 134 is first positioned on one or more, preferably two or more, pins 146 inserted approximately along the lateral, mid-axial line of the proximal phalanx. The upper and lower jaws 138, 140 are positioned, respectively, posterior and anterior to the inserted pins 146, and secured to each other and the engaged pins by tightening of one or more vertical screws 144.

The hinge 114, including proximal and distal hinge members 116, 118, connected at pivoting joint 120, is positioned onto the proximal clamping member 134 by insertion of the proximal clamping member 134 into the cavity 131 of the proximal hinge member 116.

By X-ray analysis, preferably video, the axis of rotation of the hinge (axle) is aligned with the natural axis of rotation of the joint. Once the hinge is aligned with the axis of the joint, the relative position of the attached distal hinge member 118 is used as a guide to insert one or more pins into the distal phalanx. The distal clamping member 136 is then attached to the pins 145 and the attached distal clamping member 136 inserted into the cavity 131 of the distal hinge member 118, in a manner similar to that described above for the proximal counterparts.

Figure 31:
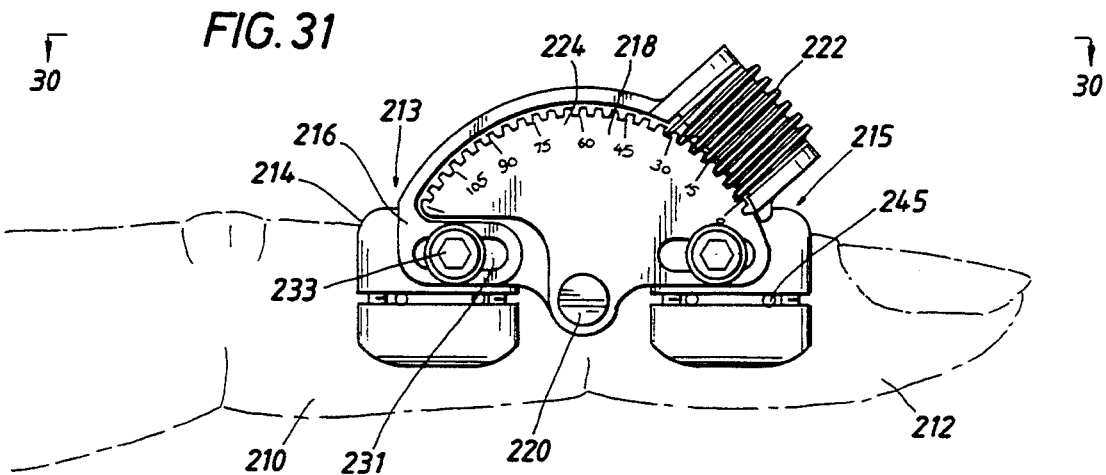
FIG. 31 is a side plan view of the embodiment of FIG. 29, showing the device in extension.
Figure 32:
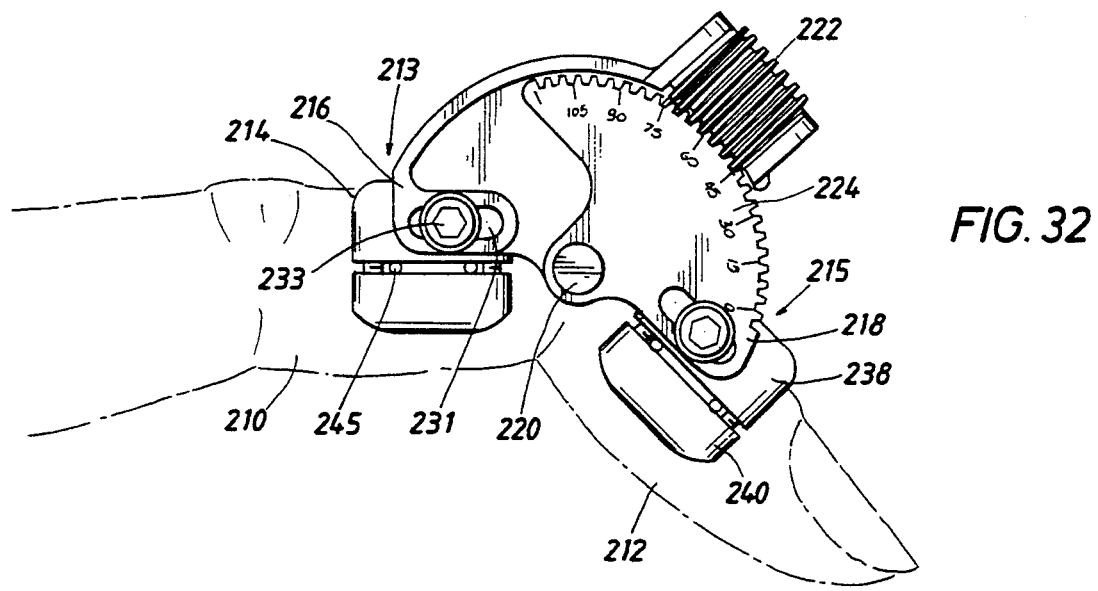
FIG. 32 is a side plan view of the embodiment of FIG. 29, showing the device in flexion.

In a most preferred embodiment, the dynamic finger support includes a unilateral hinge 214 having a first arcuate hinge member 216 and a second arcuate hinge member 218 rotatably connectable to each other, for example, as shown in FIGS. 31 and 32 by a pivoting joint 220. A radiopaque axle 221 may serve as the axis of rotation of the hinge 214 and provide a indicia means for targeting alignment of the radiotranslucent finger hinge with the natural axis of the finger joint.

This most preferred embodiment is shown as is would be connected to the finger of a patient in FIGS. 31 and 32, where reference numeral 210 identifies dashed lines illustrating the proximal phalanx of the patient's finger and 212 the distal phalanx. The dynamic finger support includes proximal and distal external support sections 213, 215, each of which is adapted for attached to pins 245 or wires (not shown) embedded in the skeletal elements of the proximal and distal phalanges 210, 212. For example, as shown in FIGS. 31 and 32, each support section 213, 215 includes superior and inferior clamping jaws 238, 240, which are joined and tightened, for example, by vertical screws 244 on the engaged pins 245. One or more vertical screws 244 may be positioned in the external support section away from the engaged pins 245.

Figure 29:
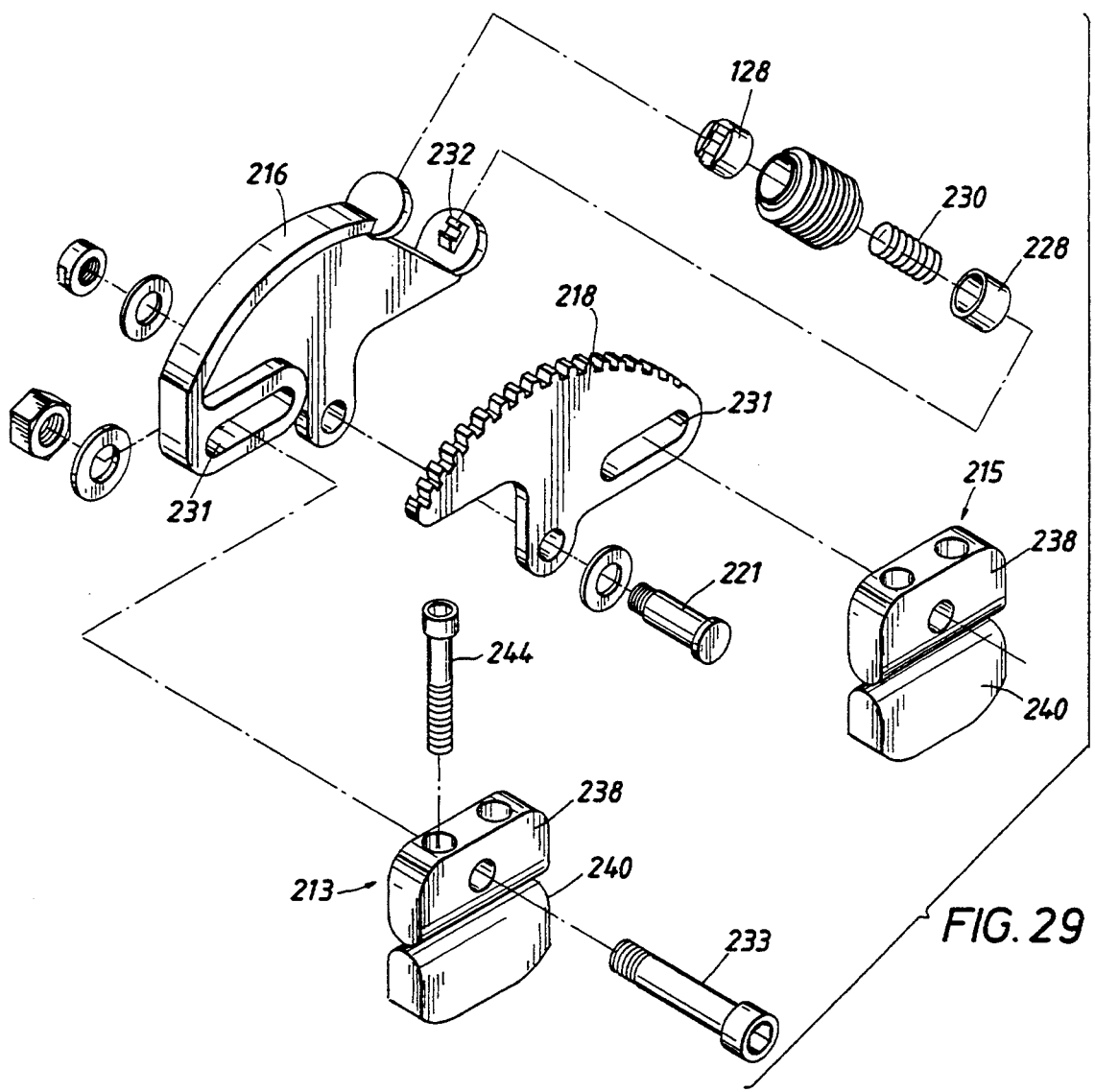
FIG. 29 is an exploded view of a most preferred embodiment of the invention.

Each arcuate hinge member 216, 218 is adapted to engage its respective external support section 213, 215. For example, as shown in FIGS. 29, 31 and 32, each arcuate hinge member 216, 218 is fastened to its respective external support section 213, 215 by a fastener, e.g., horizontal screw 233 which traverses a slot 231 in the arcuate hinge member 216, 218 to engage and fasten the arcuate hinge member to its respective external support section 213, 215. Adjustments in a proximal-distal direction to the alignment of the hinge device with respect to the natural axis of the joint may be achieved by adjusting the arcuate hinge member proximally and/or distally with respect to the horizontal screw 233.

A gear means is provided to move the proximal and distal arcuate hinge members 216, 218 their attached external support sections, 213, 215, and thereby the attached proximal and distal skeletal elements relative to each other and about the axle 221. For example, as shown best in FIGS. 31 and 32, the proximal arcuate hinge member 216 includes a worm 222 which mates with teeth 224 on the distal arcuate hinge member 218. When rotated, the worm 222 translates rotational energy to the engaged teeth 224 and thus effects extension and flexion of the finger joint of the patient.

Figure 33:
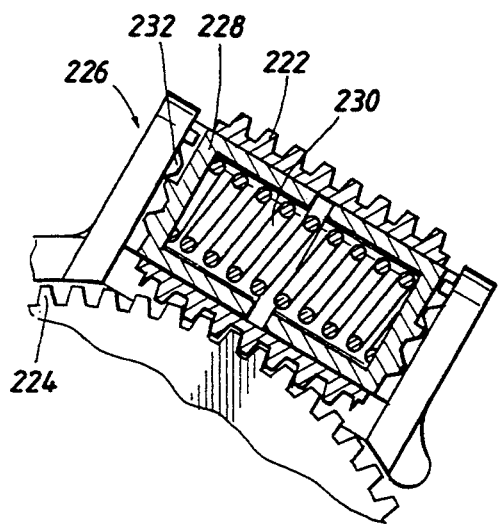
FIG. 33 is a plan view partially in section showing the gear of the device in an engaged position.
Figure 34:
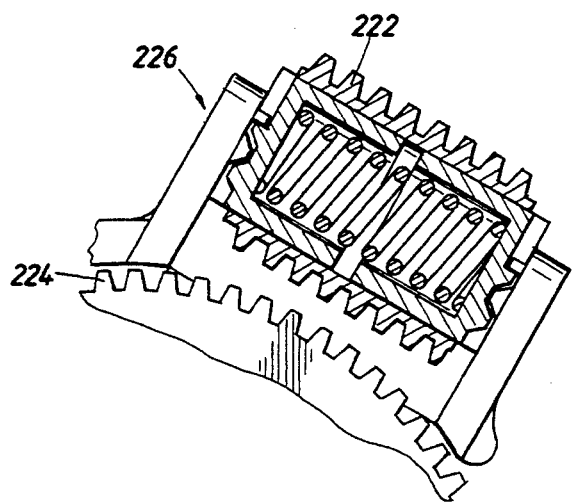
FIG. 34 is a plan view partially in section showing the gear of the device in a disengaged position.

A clutch means is further provided for permitting selective engagement of the worm 222 and teeth 224, such that force is transferred between the worm 222 and teeth 224, restricting free motion of the skeletal elements and permitting controlled motion of the joint and for selectively disengaging the worm 222 and teeth 224 to permit the skeletal elements to move freely. As shown best in FIGS. 33 and 34, the worm 222 is adjustable within the worm housing 226 to alternative fixed positions, engaged (FIG. 33) or disengaged (FIG. 34). Preferably, the worm 222 includes endcaps 228 and a deformable spring 230 to facilitate movement of the worm 222 with respect to formations 232 on the engaging surface of the worm housing 226.

Figure 30:
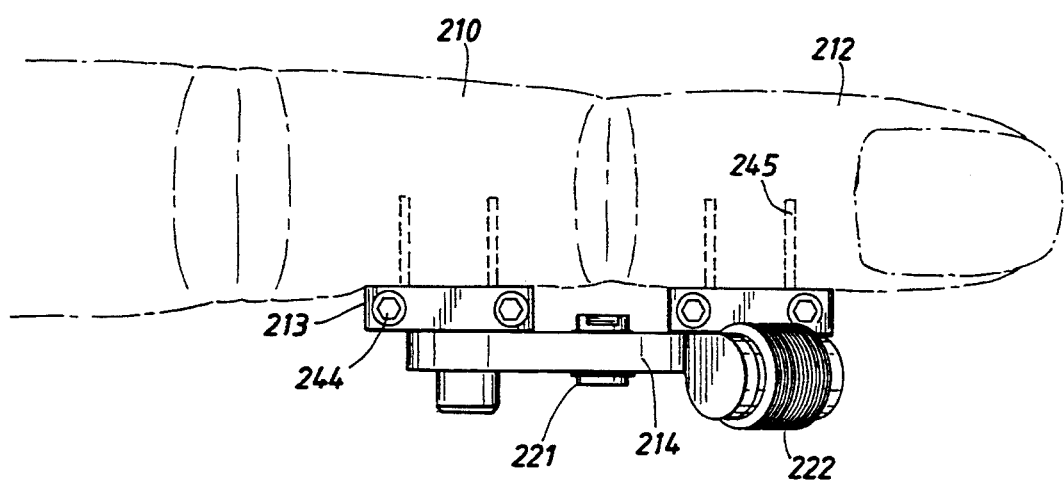
FIG. 30 is a top plan view, partially in section, of the embodiment of FIG. 29.

Referring to FIGS. 29 and 30, the installation of the dynamic finger support described above is shown. The proximal external support section 213 is first positioned on one or more, preferably two or more, pins 245 inserted approximately along the lateral, mid-axial line of the proximal phalanx. The superior and inferior clamping jaws 238, 240 are positioned, respectfully, posterior and anterior to the inserted pins 245, and secured to each other and the engaged pins by tightening of one or more vertical screws 244.

The hinge 214, including first and second arcuate hinge members 216, 218 connected at pivoting joint 220, is positioned first onto the proximal external support section 213 and secured thereto by horizontal screws 233.

By X-ray analysis, preferably video, the axis of rotation of the hinge as targeted by the radiopaque indicia, e.g., axle, is aligned with the natural axis of the joint. Once the hinge is aligned with the axis of the joint, the relative position of the attached second arcuate hinge member 218 is used as a guide to insert one or more pins into the distal phalanx. The distal external support section 215 is then attached to the pins 245 and the attached second arcuate hinge member 218 is secured to the distal external support section 215 by horizontal screws 233.

Once the finger support is attached to the finger, adjustments may be made to further refine or correct the alignment of the axis of rotation of the hinge with the natural axis of the joint. The location of the clamping members 134, 136 within the hinge members 116, 118 may be adjusted in three planes, anterior-posterior (arrow 180), proximal-distal (arrow 182), and tilted within the hinge members 116, 118 (arrow 184), i.e. to compensate for pin insertions which deviate from substantially parallel to the mid-axial line.

Distraction of the joint may be desired in treatment of injuries to the joint itself. Distraction of the PIP joint, for example, may be accomplished by manually pulling the digit in a distal direction prior to securing the hinge to the distal clamping member 136. While the joint is distracted in this manner, the distal hinge member 118 is secured to the distal clamping member 136. The attached hinge functions through its range of motion while the joint remains distracted.

It is contemplated that various sizes of the device will be preferable for various applications, e.g., when treating the finger of a child versus an adult, when treating the fourth digit versus the first.

Through the mechanism described, the dynamic finger support can be accurately aligned with the kinematic axis of the finger joint through the use of an X-ray machine, for example, by aligning a metal axle 121, or other radiopaque targeting device of the pivoting mechanical hinge 120, with the natural axis of the joint. Fine adjustments can be made by adjusting the position of the hinge members in the hinge members, as described above. Once the dynamic finger brace is accurately aligned in the preferred position, a patient can have his or her finger joint extended or flexed through the application of manual movement to the gearing mechanism. The dynamic joint brace of the present invention is useful in the treatment of trauma to a joint such as severe fractures, dislocations and the like where a high possibility of stiffness normally results from immobilization. The apparatus may be applied to the patient immediately to begin rehabilitation and prevent contracture. In some instances, it may be desirable to apply distraction to reduce the joint reaction force during flexion and extension. The dynamic brace allows for all of these treatments to occur through apparatus which is connected to bones on opposite sides of the joint and at a distance from the joint so as not to interfere with movement and rehabilitation.

The dynamic joint brace of the present invention also permits readjustments as needed during therapy without significant interference using external adjustment mechanisms. Adjustments may be necessary if the patient should fall or otherwise disturb the set alignment during therapy. Alternatively, the device permits monitored therapy, with immediate and easily accomplished adjustments in the proper alignment. Where appropriate, adjustments may be made in rotation, anterior-posterior positioning, and distal-proximal positioning of the hinge relative to the fixed skeletal elements.

The dynamic joint brace of the present invention may be fabricated using materials known in the field. It is important that the device be substantially radiotranslucent with a radio opaque targeting means at the axis of mechanical rotation to permit alignment of the axis of rotation of the hinge with the natural axis of rotation of the joint. It is preferred that the materials used to fabricate the device permit sterilization of the device. It is contemplated that portions of the device may be prepared from molds, i.e., the finger dial, shaft, and gear drive may be molded as one piece, or the rotating member may be molded as one piece including the half gear.

The foregoing description is considered to be illustrative and not limiting and variations and improvements to the invention can be made without departing from the spirit and scope of the invention. All such variations and improvements are contemplated as falling within the scope of the appended claims, which:

We claim:

1. A dynamic finger support comprising:
   proximal and distal external support sections, one for each skeletal element on opposite sides of a finger joint;
   connecting means for rigidly connecting each support section to a bone on its respective side of the joint, wherein said connecting means attaches each support section to bone at a distance from the joint and not at the axis of rotation of the joint;
   hinge means having an axis for connecting the support sections to each other in the vicinity of the joint so the hinge means will pivot the joint when the skeletal elements move through flexion and extension,
   wherein said hinge means is a unilateral hinge including a first and second arcuate hinge member rotatably connected to each other, said first arcuate hinge member being non-movable with respect to the second arcuate hinge member and said second arcuate hinge member being adapted to move relative to the first arcuate hinge member,
   and wherein the hinge means includes a gear means including a worm movably mounted in said first arcuate hinge member, which worm mates with teeth located on said second arcuate hinge member, wherein rotation of the worm causes motion of the second arcuate hinge member relative to the first arcuate hinge member,
   and wherein the gear means further includes a clutch means for selectively engaging said gear such that force is transferred between said worm and said teeth to restrict free motion of the skeletal elements and permit controlled extension and flexion of the joint, and for selectively disengaging said worm and teeth to allow the skeletal elements to move freely.

2. The dynamic finger support of claim 1, further comprising:
   radiopaque indicia means for enabling alignment of the axis of the hinge means with the axis of the joint.

3. The dynamic finger support of claim 2, further comprising:
   adjustment means for adjusting the position and orientation of the hinge relative to the respective support sections and relative to the axis of the joint.

4. A dynamic finger support comprising:
   proximal and distal external support sections, one for each skeletal element on opposite sides of the finger joint;
   connecting means for rigidly connecting each support section to a bone on its respective side of the joint, wherein said connecting means attaches each support section to a bone at a distance from the joint and not at the axis of rotation of the joint;
   hinge means having an axis for connecting the support sections to each other in the vicinity of the joint so the hinge means will pivot the joint when the skeletal elements move through flexion and extension, wherein said hinge means is a unilateral hinge including a first and second arcuate hinge member rotatably connected to each other, said first arcuate hinge member being nonmovable with respect to said second arcuate hinge member and said second arcuate hinge member being adapted to move relative to the first arcuate hinge member, and wherein said axis of the hinge is adapted for alignment with the axis of the joint; and
   wherein the dynamic finger support is substantially radiotranslucent, and having a radiopaque indicia means for enabling alignment of the axis of the hinge means with the axis of the joint.

5. The dynamic finger support of claim 4, further comprising: adjustment means for adjusting the position and orientation of the hinge relative to the respective support sections and relative to the axis of the joint.

6. The dynamic joint support of claim 5, wherein the hinge means includes a gear means for moving the support sections and consequently their respective skeletal elements through flexion and extension in response to the application of external force to the gear means.

7. The dynamic joint support of claim 6, wherein said gear means includes a drive means movably mounted in said first arcuate hinge member, which drive means mates with teeth located on said second arcuate hinge member, wherein rotation of the drive means causes motion of the second arcuate hinge member relative to the first arcuate hinge member, thereby causing flexion or extension of the attached skeletal elements.

8. The dynamic joint support of claim 7, wherein the gear means further includes a clutch means selectively engaging said gear such that force is transfer between said worm and said teeth to restrict free motion of skeletal elements and permit controlled extension and flexion the joint, and for selectively disengaging said worm and teeth allow the skeletal elements to move freely.

9. A dynamic finger support comprising:

proximal and distal external support sections, one for each skeletal element on opposite sides of the finger joint;

connecting means for rigidly connecting each support section to a bone on its representative side of the joint, wherein said connecting means attaches each support section to bone at a distance from the joint and not at the axis of rotation of the joint;

hinge means having an axis for connecting the support sections to each other in the vicinity of the joint so the hinge means will pivot the joint when the skeletal elements move through flexion and extension, wherein said hinge means is a unilateral hinge including a first and second arcuate hinge member rotatably connected to each other, said first arcuate hinge member being non-movable with respect to said second arcuate hinge member and said second arcuate hinge member being adapted to move relative to the first arcuate hinge member, and wherein the hinge means includes a gear means for moving the support sections and consequently their respective skeletal elements through flexion and extension in response to the application of external force to the gear means, said gear means including a worm movably mounted in said first arcuate hinge member, which worm mates with teeth located on said second arcuate hinge member, wherein rotation of the worm causes motion of the second arcuate hinge member relative to the first arcuate hinge member thereby causing flexion or extension of the attached skeletal elements;

adjustment means for adjusting the position and orientation of the hinge relative to the respective support sections and relative to the axis of the joint; and radiopaque indicia means for enabling alignment of the axis of the hinge means with the axis of the joint.

10. A dynamic joint support comprising:

proximal and distal external support sections, one for each skeletal element on opposite sides of the joint;

connective means for rigidly connecting each support section to a bone on its respective side of the joint, wherein said connecting means attach each support section to a bone at a distance from the Joint and not at the axis of rotation of the joint;

hinge means having an axis for connecting the support sections to each other in the vicinity of the joint so the hinge means will pivot the Joint when the skeletal elements move through flexion and extension, wherein said hinge means includes a first and a second hinge member rotatably connected to each other at a pivot, which pivot forms the axis of the hinge, said first hinge member being nonmovable with respect to the second hinge member and said second hinge member being adapted to move relative to the first hinge member, and wherein said hinge means is unilateral.

11. The dynamic joint support of claim 10, wherein the hinge means further includes:

gear means for moving the support sections and consequently their respective skeletal elements through flexion and extension in response to the application of external force to the gear means.

12. The dynamic Joint support of claim 11, wherein the gear means includes a drive means movably mounted in said first hinge member, which drive means mates with teeth located on said second hinge member, wherein rotation of the drive means causes motion of the second hinge member relative to the first hinge member.

13. The dynamic Joint support of claim 12, further comprising a clutch means for selectively engaging said gear means such that force is transferred between the drive means and the teeth to restrict free motion of the skeletal elements and permit controlled extension and flexion of the joint, and for selectively disengaging the drive means and teeth to allow the skeletal elements to move freely.

14. The dynamic joint support of claim 10, further comprising adjustment means for adjusting the position and orientation of the hinge relative to the respective support sections and relative to the axis of the joint.

15. The dynamic joint support of claim 14, wherein said adjustment means permits adjustment of the position and orientation of the hinge relative to the axis of the joint after the external support sections have been fixed to the skeletal elements.

16. The dynamic joint support of claim 14, wherein adjustment means permits adjustment in two or more directional planes.

17. The dynamic joint support of claim 10, further comprising indicia means for enabling alignment of the axis of the hinge means with the natural axis of the joint.

18. The dynamic joint support of claim 17, wherein the support is substantially radiotranslucent and wherein the indicia means is radiopaque.

* * * * *